United States Patent [19]

Pappo et al.

[11] 4,003,996
[45] Jan. 18, 1977

[54] SPIROLACTONE FOR INHIBITING THE CARDIOTOXIC EFFECTS OF ADRIAMYCIN

[75] Inventors: Raphael Pappo, Skokie; Rothwell Polk, Northfield, both of Ill.

[73] Assignee: G. D. Searle & Co., Chicago, Ill.

[22] Filed: Sept. 9, 1974

[21] Appl. No.: 504,095

[52] U.S. Cl. .............................. 424/181; 424/240
[51] Int. Cl.² ...................................... A61K 31/71
[58] Field of Search ........................... 424/240, 181

[56] References Cited

OTHER PUBLICATIONS

Lefrak et al., Cancer, vol. 32, Aug. 1973, pp. 302–314.
O'Bryan et al., Cancer, vol. 32, July 1973, pp. 1–8.
Chemical Abstracts 73: 21854d (1970).

Primary Examiner—Jerome D. Goldberg
Attorney, Agent, or Firm—Elliot N. Schubert; John J. McDonnell

[57] ABSTRACT

The administration of aldosterone inhibitors of the spirolactone structural type prior to and during treatment with anti-neoplastic agents such as adriamycin results in retention of the desired activity of the latter substances while inhibiting their undesirable cardiotoxic properties.

1 Claim, No Drawings

SPIROLACTONE FOR INHIBITING THE CARDIOTOXIC EFFECTS OF ADRIAMYCIN

Contemplated by the present invention is a method for treating neoplastic states, particularly those of the malignant type by pretreatment with spironolactone prior administering adriamycin.

Anti-neoplastic agent such as adriamycin is useful in the treatment of tumorous conditions, but, as is pointed out and discussed by Adamson, Cancer Chemotherapy Reports, Part 1, Vol. 58, No. 3, May/June 1974, suffer from a number of disadvantages, among which is their tendency to cause severe, irreversible and undesirable effects on the heart muscle. This cardiac myopathy, in many cases, leads to irreversible congestive heart failure. Rabbit studies carried out by Olson, Le Ray and Munroe, Proc. Am. Assoc. Cancer Res., 15, 103(1974) indicate that adriamycin may exert its detrimental effect by interference with the electrolyte balance through the mechanism of altering membrane permeability, thereby resulting in the development of characteristic microscopic lesions, such as myocytolysis, edema and fibrosis. Studies by Rosenoff, Brooks, Bostick, De Vita and Young, Proc. Am. Assoc. Cancer Res., 15, 38(1974) suggest that adriamycin-induced cardiac myopathy may be related to the reduction of desoxyribonucleic acid synthesis in the heart.

It has surprisingly been found that aldosterone antagonists, in particular those having the steroidal spirolactone structure as hereinbefore defined, have the capability of preventing the cardiac side-effects exhibited by the anti-neoplastic agents discussed above. This discovery affords the particular advantage of allowing larger dosages of the anti-neoplastic agent to be used, thereby enhancing their utility. The ultimate beneficial effects thus are prolongation of the life of the animal species and amelioration of the disease state.

An aldosterone antagonist suitable for use in the present invention is Aldactone(spironolactone) 3-(3-oxo-7α-acetylthio-17β-hydroxyandrost 4-en-17α-yl)propionic acid γ-lactone.

It is apparent from the above recitation and the exemplification included therein that not only the spironolactone, but also the corresponding hydroxy acids and ammonium and alkali metal and alkaline earth metal salts thereof are operable in the present invention.

The spirolactone and the corresponding hydroxy acids and ammonium, alkali metal and alkaline earth metal salts thereof of the present invention are utilized in amounts suitable to achieve the desired purpose, i.e. that amount which will inhibit the undesirable cardiotoxic effects of the anti-neoplastic agents of this invention while not affecting their anti-tumor effect. A total daily dosage within the range of 25–1000 mg. of the aldosterone inhibitor is suitable for the purposes of this invention. A particularly preferred range is 150–600 mg. administered daily.

The aldosterone inhibitors can be administered either orally or parenterally, e.g. intravenously, depending upon their solubility in aqueous systems. Thus, the lactones are preferably administered orally while the hydroxy acids and salts thereof, by virtue of their greater water-solubility can be administered either orally or parenterally.

The anti-neoplastic agent is preferably administered intravenously at an appropriate time following pre-administration of the aldosterone inhibitor. The aldosterone inhibitor and anti-neoplastic agent are then administered concomitantly over the course of treatment and administration of the aldosterone inhibitor is continued for a brief period following cessation of treatment with the anti-neoplastic agent. Thus, for example, Aldactone is administered orally at the indicated dose for a period of 72 hours, at the end of which time adriamycin therapy is commenced. Adriamycin, at the rate of 0.7 mg/kg. body weight, is given once every 3 weeks until a total cumulative dose of 550 mg/square meter body surface is achieved. During this course of treatment, Aldactone at the indicated dose, preferably within the range of 150–600 mg., is taken orally. The latter therapy is then continued for an additional 72 hours to ensure inhibition of the cardiotoxic effects of the anti-neoplastic agent.

What is claimed is:

1. A method for inhibiting the cardiotoxic effects of adriamycin in an animal which comprises pretreating said animal with the aldosterone inhibitor 3-(3-oxo-7α-acetylthio-17β-hydroxyandrost-4-en-17-yl)propionic acid lactone in an amount sufficient to inhibit said effects prior to treatment with adriamycin.

* * * * *